United States Patent
Dominici et al.

(10) Patent No.: US 10,647,997 B2
(45) Date of Patent: May 12, 2020

(54) MODIFIED EFFECTOR CELL (OR CHIMERIC RECEPTOR) FOR TREATING DISIALOGANGLIOSIDE $G_{D2}$-EXPRESSING NEOPLASIA

(71) Applicants: Massimo Dominici, Ferrara (IT); Sara Caldrer, San Pietro in Cairano (IT); Maria Carlotta Spano, Modena (IT); Paolo Paolucci, Bologna (IT); Marco Bestagno, Trieste (IT); Dario Campana, Singapore (SG)

(72) Inventors: Massimo Dominici, Ferrara (IT); Sara Caldrer, San Pietro in Cairano (IT); Maria Carlotta Spano, Modena (IT); Paolo Paolucci, Bologna (IT); Marco Bestagno, Trieste (IT); Dario Campana, Singapore (SG)

(73) Assignee: St. Jude Children's Research Hospital, Inc., Memphis, TN (US)

( * ) Notice: Subject to any disclaimer, the term of this patent is extended or adjusted under 35 U.S.C. 154(b) by 24 days.

(21) Appl. No.: 14/354,082

(22) PCT Filed: Oct. 25, 2012

(86) PCT No.: PCT/IB2012/055878
§ 371 (c)(1),
(2) Date: Apr. 24, 2014

(87) PCT Pub. No.: WO2013/061273
PCT Pub. Date: May 2, 2013

(65) Prior Publication Data
US 2014/0302608 A1 Oct. 9, 2014

(30) Foreign Application Priority Data
Oct. 25, 2011 (IT) .............................. MO2011A0270

(51) Int. Cl.
| | | |
|---|---|---|
| *C12N 15/85* | (2006.01) | |
| *A61K 35/17* | (2015.01) | |
| *C07K 14/705* | (2006.01) | |
| *C07K 14/47* | (2006.01) | |
| *C07K 16/42* | (2006.01) | |
| *C07K 16/30* | (2006.01) | |

(52) U.S. Cl.
CPC .............. *C12N 15/85* (2013.01); *A61K 35/17* (2013.01); *C07K 14/4748* (2013.01); *C07K 14/70517* (2013.01); *C07K 16/3084* (2013.01); *C07K 16/4266* (2013.01); *C07K 2317/622* (2013.01); *C07K 2319/00* (2013.01)

(58) Field of Classification Search
CPC .................................................... C12N 15/85
See application file for complete search history.

(56) References Cited

U.S. PATENT DOCUMENTS

2005/0113564 A1* 5/2005 Campana ......... C07K 14/70517
530/350
2014/0004132 A1 1/2014 Brenner et al.

FOREIGN PATENT DOCUMENTS

WO 2005044996 5/2005

OTHER PUBLICATIONS

Pule et al. (2008, Nature Med., vol. 14(11), pp. 1264-1270).*
Rossig et al. (2002, Blood, vol. 99(6), pp. 2009-2016).*
Cheresh et al. (1986, JBC, vol. 102, pp. 688-696).*
Cho et al. (2009, Korean J. Lab Med., vol. 29(2), pp. 89-96).*
Wajchman et al. (2004, Cancer Research, vol. 64, pp. 1171-1180) (Year: 2004).*
Panwala L. (2017, PEDIAA, Differences Between NK Cells and NKT Cells, pp. 1-6). (Year: 2017).*
Richman et al. (2018, Cancer Immunol. Res., vol. 6(1), pp. 36-46) (Year: 2018).*
Martin A Pule et al: "Virus-specific T cells engineered to coexpress tumor-specific receptors: persistence and antitumor activity in individuals with neuroblastoma", Nature Medicine, vol. 14, No. 11, Nov. 1, 2008 (Nov. 1, 2008), pp. 1264-1270, XP55021755, ISSN: 1078-8956, DOI: 10.1038/nm.1882 p. 1265, col. 1, paragraph 1—p. 1266, col. 1, paragraph 1; p. 1267, col. 1, paragraph 1; p. 1268, col. 2, paragraph 2.
Imai C et al: "Chimeric receptors with 4-1BB signaling capacity provoke potent cytotoxicity against acute lymphoblastic leukemia", Leukemia, Macmillan Press Ltd, US, vol. 18, No. 4, Apr. 1, 2004 (Apr. 1, 2004), pp. 676-684, XP002579934, ISSN: 0887-6924 p. 676, col. 2; p. 682, col. 2—p. 683, col. 1.
Eshhar Z et al: "Specific Activation and Targeting of Cytotoxic Lymphocytes Through Chimeric Single Chains Consisting of Antibody-Binding Domains and the Gamma or Zeta Subunits of the Immunoglobulin and T-Cell Receptors", Proceedings of the National Academy of Sciences of USA, National Academy of Science, Washington, DC; US, vol. 90, No. 2, Jan. 15, 1993 (Jan. 15, 1993), pp. 720-724, XP002009770, ISSN: 0027-8424, DOI: 10.1073/PNAS.90.2.720.
B. Jena et al: "Redirecting T-cell specificity by introducing a tumor-specific chimeric antigen receptor", Blood, vol. 116, No. 7, Aug. 19, 2010 (Aug. 19, 2010), pp. 1035-1044, XP55021403, Issn: 0006-4971, DOI: 10.1182/blood-2010-01-043737 p. 1035, col. 2, paragraph 2; p. 1037, col. 1, paragraph 1; p. 1038, col. 2—p. 1039, col. 1.

(Continued)

*Primary Examiner* — Thaian N. Ton
*Assistant Examiner* — David A. Montanari
(74) *Attorney, Agent, or Firm* — Themis Law; Franco A. Serafini; David M. Fortner (57) ABSTRACT

A modified effector cell includes a non-reversibly produced vector-encoded anti-$G_{D2}$-BB-ζ chimeric receptor for use in disialoganglioside $G_{D2}$-expressing neoplasia, which is inserted in the cell, to obtain an effector cell that stably produces the anti-$G_{D2}$-BB-ζ chimeric receptor, the chimeric receptor having two distinct mutually fused portions, i.e. an intra-cytoplasmic portion and an extra-cytoplasmic portion.

8 Claims, 10 Drawing Sheets

Specification includes a Sequence Listing.

(56) References Cited

OTHER PUBLICATIONS

Xiaocai Yan et al: "Murine CD8 lymphocyte expansion in vitro by artificial antigen-presenting cells expressing CD137L (4-1BBL) is superior to CD28, and CD137L expressed on neuroblastoma expands CD8 tumour-reactive effector cells in vivo", Immunology, vol. 112, No. 1, May 1, 2004 (May 1, 2004), pp. 105-116, XP55021880, ISSN: 0019-2805, DOI: 10.1111/j.1365-2567.2004.01853.x p. 106, col. 1, paragraph 2; p. 113, col. 1, paragraph 1; p. 114, col. 1, paragraph 1.
Ramos CA, Dotti G. Chimeric antigen receptor (CAR)-engineered lymphocytes forcancer therapy. Expert Opin Biol Ther. Jul. 2011;11(7):855-73.
Cheresh DA, Pierschbacher MD, Herzig MA, Mujoo K. Disialogangliosides GD2 and GD3 are involved in the attachment of human melanoma and neuroblastoma cells to extracellular matrix proteins. J Cell Biol. Mar. 1986;102(3):688-96.
Sadelain M, Brentjens R, Rivière I. The promise and potential pitfalls of chimeric antigen receptors. Curr Opin Immunol. Apr. 2009;21(2):215-23.
Krause A, Guo HF, Latouche JB, Tan C, Cheung NK, Sadelain M. Antigen-dependent CD28 signaling selectively enhances survival and proliferation in genetically modified activated human primary T lymphocytes. J Exp Med. Aug. 17, 1998;188(4):619-26.
Rossig C, Bollard CM, Nuchtern JG, Merchant DA, Brenner MK. Targeting of G(D2)-positive tumor cells by human T lymphocytes engineered to express chimeric T-cell receptor genes. Int J Cancer. Oct. 15, 2001;94(2):228-36.
López-Requena A, Bestagno M, Mateo De Acosta C, Cesco-Gaspere M, Vazquez AM, Perez R, Burrone OR. Gangliosides, Ab1 and Ab2 antibodies III. The idiotype of anti-ganglioside mAb P3 is immunogenic in a T cell-dependent manner. Mol Immunol. Apr. 2007;44(11):2915-22.
López-Requena A, Mateo De Acosta C, Bestagno M, Vazquez Am, Perez R, Burrone OR. Gangliosides, Ab1 and Ab2 antibodies IV. Dominance of VH domain in the induction of anti-idiotypic antibodies by gene gun immunization. Mol Immunol. Apr. 2007;44(11):3070-5. Epub Mar. 2, 2007.
Nakamura K, Koike M, Shitara K, Kuwana Y, Kiuragi K, Igarashi S, Hasegawa M, Hanai N. Chimeric anti-ganglioside GM2 antibody with antitumor activity. Cancer Res. Mar. 15, 1994;54(6):1511-6.
Imai C, Mihara K, Andreansky M, Nicholson IC Pui, C-H, Geiger TL and Campana D. Chimeric receptor with 4-1BB signalling capacity provoke potent cytotoxicity againsta acute lymphoblastic leukemia. Leukemia (2004) 8, 676-684.
Kim YJ, Kim SH, Mantel P, Kwon BS. Human 4-1BB regulates CD28 co-stimulation to promote Th1 cell responses. Eur J Immunol 1998; 28: 881-890.
Hurtado JC, Kim YJ, Kwon BS. Signals through 4-1BB are costimulatory to previously activated splenic T cells and inhibit activation-induced cell death. J Immunol 1997; 158: 2600-2609.
Debenedette MA, Shahinian A, Mak TW, Watts TH. Costimulation of CD28 T lymphocytes by 4-1BB ligand. J Immunol 1997; 158: 551-559.
Bukczynski J, Wen T, Watts TH. Costimulation of human CD28 T cells by 4-1BB ligand. Eur J Immunol 2003; 33: 446-454.
Walter W. Shuford, Kerry Klussman, Douglas D. Tritchler, Deryk T. Loo, Jan Chalupny, Anthony W. Siadak, T. Joseph Brown, John Emswiler, Hong Raecho, Christian P. Larsen, Thomas C. Pearson, Jeffrey A. Ledbetter, Alejandro Aruffo and Robert S. Mittler. 4-1BB costimulatory signals preferentially induce CD8+ T cell proliferation and lead to the amplification in vivo of cytotoxic T cell responses. J Exp Med 1997; 186: 47-55.
Takahashi C, Mittler RS, Vella AL Cutting edge: 4-1BB is a bona fide CD8 T cell survival signal. J Immunol 1999; 162: 5037-5040.
Martinet O, Divino CM, Zang Y, Gan Y, Mandeli J, Thung S Mandeli J, Thung S., Pan P-Y and Chen S-H. T cell activation with systemic agonistic antibody vs local 4-1BB ligand gene delivery combined with interleukin-12 eradicate liver metastases of breast cancer. Gene Ther 2002; 9: 786-792.
May JR KF, Chen L, Zheng P, Liu Y. Anti-4-1BB monoclonal antibody enhances rejection of large tumor burden by promoting survival but not clonal expansion of tumor-specific CD8+ T cells. Cancer Res 2002; 62: 3459-3465.
Melero I, Shuford WW, Newby SA, Aruffo A, Ledbetter JA, Hellstrom KE, Ledbetter A., Hellström K.E., Robert S. Chen ML. Monoclonal antibodies against the 4-1BB T-cell activation molecule eradicate established tumors. Nat Med 1997; 3: 682-685.
Melero I, Bach N, Hellstrom KE, Aruffo A, Mittler RS, Chen L. Amplification of tumor immunity by gene transfer of the costimulatory 4-1BB ligand: synergy with the CD28 co-stimulatory pathway. Eur J Immunol 1998; 28: 1116-1121.
Ye Z, Hellstrom I, Hayden-Ledbetter M, Dahlin A, Ledbetter JA, Hellstrom KE. Gene therapy for cancer using single-chain Fv fragments specific for 4-1BB. Nat Med 2002; 8: 343-348.
Mogi S, Sakurai J, Kohsaka T, Enomoto S, Yagita H, Okumura K. and Azuma M. Tumour rejection by gene transfer of 4-1BB ligand into a CD80(+) murine squamous cell carcinoma and the requirements of co-stimulatory molecules on tumour and host cells. Immunology 2000; 101: 541-547.
Yoshida H, Katayose Y, Unno M, Suzuki M, Kodama H, Takemura S, Asano R, Hayashi H, Yamamoto K, Matsuno S, Kudo T. A novel adenovirus expressing human 4-1BB ligand enhances antitumor immunity. Cancer Immunol Immunother 2003; 52: 97-106.
Porter DL, Levine BL, Kalos M, Bagg A, June CH, Chimeric Antigen Receptor-Modified T Cells in Chronic Lymphoid Leukemia, N Engl J Med 2011, 365:725-733.
Wajchman HJ, Pierce CW, Varma VA, Issa MM, Petros J, Dombrowski KE, Ex vivo expansion of CD8+ CD56+ and CD8+ CD56– natural killer T cells specific for MUC1 mucin, Cancer Res. 2004; 64:1171-80.
Long, A. et al., 4-1BB Costimulation Ameliorates T Cell Exhaustion Induced by Tonic Signaling of Chimeric Antigen Receptors, Nat. Med. Jun. 2015; 21(6): 581-590.
Tian. G. et al., CD62L+ NKT cells have prolonged persistence and antitumor activity in vivo, Clin. Invest. 2016; 126(6), 2341-2355 (2016).
Smyth, M. et al, Differential Tumor Surveillance by Natural Killer (NK) and NKT Cells, J. Exp. Med., vol. 191, No. 4, Feb. 21, 2000 661-668 (2000).

\* cited by examiner

FIG. 1C

Table 1 | Tumour antigens targeted by genetically modified primary T cells

| Target antigen | Associated malignancy | Receptor type | In vivo studies | References |
|---|---|---|---|---|
| MDM2 | Multiple malignancies | αβ TCR | – | 15 |
| MART1 | Melanoma | αβ TCR | – | 14 |
| MAGE-A1 | Melanoma | αβ TCR | | 21 |
| LMP2 | Type II EBV+ tumours | αβ TCR | – | 16 |
| CD30 | Lymphomas | scFv-FcεRγ | – | 48 |
| ERBB2,3,4 | Breast and others | Heregulin-CD3ζ | – | 24,25 |
| | | scFv-CD3ζ | + | 30 |
| CEA | Colorectal cancer | scFv-CD3ζ | + | 46,47,119,120 |
| | | scFv-FcεRγ | + | 31,46 |
| | | scFv-CD3ε | – | 44 |
| EGP40 | Colorectal cancer | scFv-FcεRγ | – | 121 |
| TAG-72 | Adenocarcinomas | scFv-CD3ζ | + | 33,122 |
| GD3 | Melanoma | scFv-CD3ζ | – | 123 |
| | | scFv-CD3ε | – | 123 |
| PSMA | Prostate cancer | scFv-CD3ζ | – | 64 |
| FBP | Ovarian cancer | scFv-FcεRγ | + | 34,35,124 |
| G250 | Renal-cell carcinoma | scFv-FcεRγ | – | 125–127 |
| EGP2 | Multiple malignancies | scFv-CD3ζ | – | 42 |
| | | scFv-FcεRγ | – | 42,128 |
| GD₂ | Neuroblastoma | scFv-CD3ζ | – | 41 |
| CD19 | B-cell malignancies | scFv-CD3ζ | + | 36 |
| PSMA | Tumour neovasculature | scFv-CD3ζ | – | 64 |
| KDR | Tumour neovasculature | scFv-FcεRγ | – | 129 |
| VEGF-R2 | Tumour neovasculature | scFv-CD3ζ | – | 130 |
| GD₂ | Neuroblastoma | scFv-CD28 | – | 40 |
| CEA | Colorectal cancer | scFv-CD28-CD3ζ | – | 38 |
| PSMA | Prostate/tumour vasculature | scFv-CD28-CD3ζ | – | 65 |
| ERBB2 | Breast and others | scFv-CD28-CD3ζ | + | 32 |

FIG. 1D

Table 1. CLINICAL TRIALS OF MONOCLONAL ANTIBODY-BASED IMMUNOTHERAPY IN PATIENTS
WITH RELAPSED OR REFRACTORY NEUROBLASTOMA

| Study | Monoclonal Antibody (mg/m²/course) | Cytokines | No. of Patients Evaluable for Response | Responses |
|---|---|---|---|---|
| *Phase I studies* | | | | |
| Cheung (1987)[12, 11] | 3F8 (5-100) | — | 6 | 1 PR, 2 SD, 3 PD |
| Huang (1992)[23] | 14G2a (25-500) | — | 15 | 1 CR, 3 MR, 1 SD |
| Handgretinger (1992)[25] | 14G2a (100-400) | — | 6 | 2 CR, 2 PR, 2 PD |
| Murray (1994)[10] | 14G2a (50-200) | — | 5 | 2 PR, 1 SD, 2PD |
| Frost (1997)[22] | 14G2a (10-100) | IL-2+GM-CSF | 31* | 1 PR, 7 SD |
| Handgretinger (1995)[24] | ch14.18 (150-250) | — | 9 | 2 CR, 2 PR, 1 MR, 1 SD, 3 PD |
| Yu (1998)[13] | ch14.18 (10-200) | — | 9 | 1 CR, 4 MR, 1 SD, 3 PD |
| *Phase II studies* | | | | |
| Yu (1997)[20] | ch14.18 (200) | GM-CSF | 27 | 1 CR, 3 PR, 1 MR, 2 SD |
| Cheung (1998)[16] | 3F8 (50) | — | 16 | 1 CR, 1 MR, 1 SD |
| Kushner (2001)[25] | 3F8 (100) | GM-CSF | 43 | 11 CR/VGPR†, 4 MR, 8 SD |

*Seven patients of 33 in entire study (31 neuroblastoma patients, 2 patients with osteogenic sarcoma) did not comp
†All in patients with stable/refractory (not progressive) disease at time of immunotherapy.
IL = Interleukin-2; GM-CSF = granulocyte-macrophage colony-stimulating factor; PR = partial response; SD = stable disease; CR = complete response; MR = mixed response; VGPR = very good partial response; PD = progressive disease.

Monoclonal antibody-based therapy for neuroblastoma (Current Oncology reports 2000, 2:547-553)

SEQUENCE LISTING

<160> NUMBER OF SEQ ID NOS: 2

<210> SEQ ID NO 1
<211> LENGTH: 1612
<212> TYPE: DNA
<213> ORGANISM: HOMO SAPIENS

<400> SEQUENCE: 1

```
atgggctgga gcctgatcct cctgttcctc gtcgctgtgg ctacaggtaa ggggctcaca      60
gtagcaggct tgaggtctgg acatatatat gggtgacaat gacatccact ttgcctttct     120
ctccacaggt gtgcactcgg atattgtgat gacccagtct ccatcctccc tggctgtgtc     180
agcaggagag aaggtcacta tgaactgcag atccagtcag agtctcctca gcagtagaac     240
ccgaaagaac tacttggctt ggtaccagca gaaaccaggg cagtctccta aactgctgat     300
ctactgggca tctattaggg aatctggggt ccctgatcgc ttcacaggca gtggatctgg     360
gacagatttc actctcacca tcagcagtgt gcaggctgaa gacctggcag tttattactg     420
caagcaatct tataatcttc ggacgttcgg tggaggcacc aagctggaaa tcaaaggcag     480
cactagtggt agcggcaaac aggttccggg cgaaggctcg agcaaaggtg aggtgcagct     540
```

```
gcaggagtct ggacctggcc tggtggcgcc ctcacagagc ctgtccatca cttgcactgt    600
ctctgggttt tcattaccca gctatggtgt tcactgggtt cgccagcctc caggaaaggg    660
tctggagtgg ctgggagtaa tctgggctgg tggaatcaca aattataact cggctctcat    720
gtccagactg accatcagca aagacaactc caagagccaa gttttcttaa aaatgaacag    780
tcttcaaact gatgacacag ccatatacta ctgtgccaga ggcggctctg attacgacgg    840
ctttgcttac tggggccaag ggactctggt cactgtctct accacgacgc cagcgccgcg    900
accaccaaca ccggcgccca ccatcgcgtc gcagcccctg tccctgcgcc cagaggcgtg    960
ccggccagcg gcggggggcg cagtgcacac gaggggggctg gacttcgcct gtgatatcta   1020
catctgggcg cccttggccg ggacttgtgg ggtccttctc ctgtcactgg ttatcaccct   1080
ttactgcaaa cggggcagaa agaaactcct gtatatattc aaacaaccat ttatgagacc   1140
agtacaaact actcaagagg aagatggctg tagctgccga tttccagaag aagaagaagg   1200
aggatgtgaa ctgagagtga agttcagcag gagcgcagac gccccgcgt accagcaggg    1260 ccagaaccag ctctataacg agctcaatct aggacgaaga gaggagtacg atgtttgga    1320 caagagacgt ggccgggacc ctgagatggg gggaaagccg agaaggaaga accctcagga   1380
aggcctgtac aatgaactgc agaaagataa gatggcggag gcctacagtg agattgggat   1440
gaaaggcgag cgccggaggg gcaaggggca cgatggcctt taccagggtc tcagtacagc   1500
caccaaggac acctacgacg cccttcacat gcaggccctg cccctcgct aacagccagg    1560 ggatttcacc actcaaaggc cagacctgca gacgcccaga ttatgagaca ca          1612

<210> SEQ ID NO 2
<211> LENGTH: 40
<212> TYPE: PRT
<213> ORGANISM: Homo sapiens

<400> SEQUENCE: 2

Gly Cys Cys Thr Thr Ala Ala Gly Gly Cys Thr Thr Ala Gly Cys Ala
1               5                   10                  15

Gly Thr Ala Ala Ala Gly Gly Gly Thr Gly Ala Thr Ala Ala Cys Cys
            20                  25                  30

Ala Gly Thr Gly Ala Cys Ala Gly
        35                  40
```

MODIFIED EFFECTOR CELL (OR CHIMERIC RECEPTOR) FOR TREATING DISIALOGANGLIOSIDE $G_{D2}$-EXPRESSING NEOPLASIA

FIELD OF THE INVENTION

The present invention relates to genetic modification of effector cells (EC) with an anti-$G_{D2}$-BB-ζ chimeric receptor, in short CR, which is performed ex-vivo, i.e. outside the body of the patient, and capable of recognizing the disialoganglioside $G_{D2}$ expressed by tumor cells.

INCORPORATION BY REFERENCE OF MATERIAL SUBMITTED ON A COMPACT DISK OR AS A TEXT FILE VIA THE OFFICE ELECTRONIC FILING SYSTEM

The present specification incorporates by reference the material submitted in the ASCII text file named Sequence-Listing ST25, created on Apr. 23, 2014 and having a size of 2.90 kilobytes.

BACKGROUND ART

Knowledge of cell immune function and tumor biology has shown that a competent immune system has a key role in cancer prevention and treatment.

Genetic and epigenetic events cause abnormal generation of a large number of new antigens (Ag), that are constantly produced by tumors as the latter develop and progress.

Immune system components may theoretically detect these Ags and trigger direct cell and tumor responses against the transformed cells, thereby inhibiting development thereof.

Figure 1A:
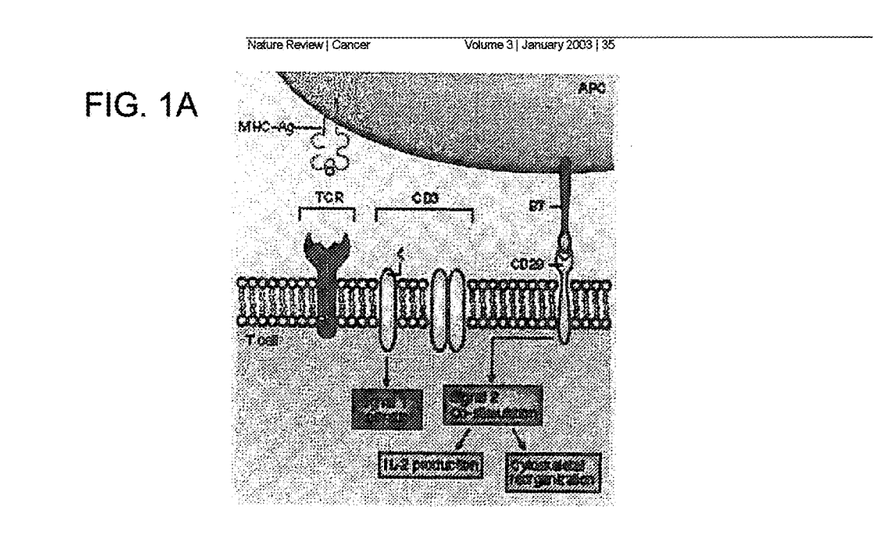
FIGS. 1A-1D illustrate different disclosures in the prior art and in the field of the present invention.
Figure 1B:
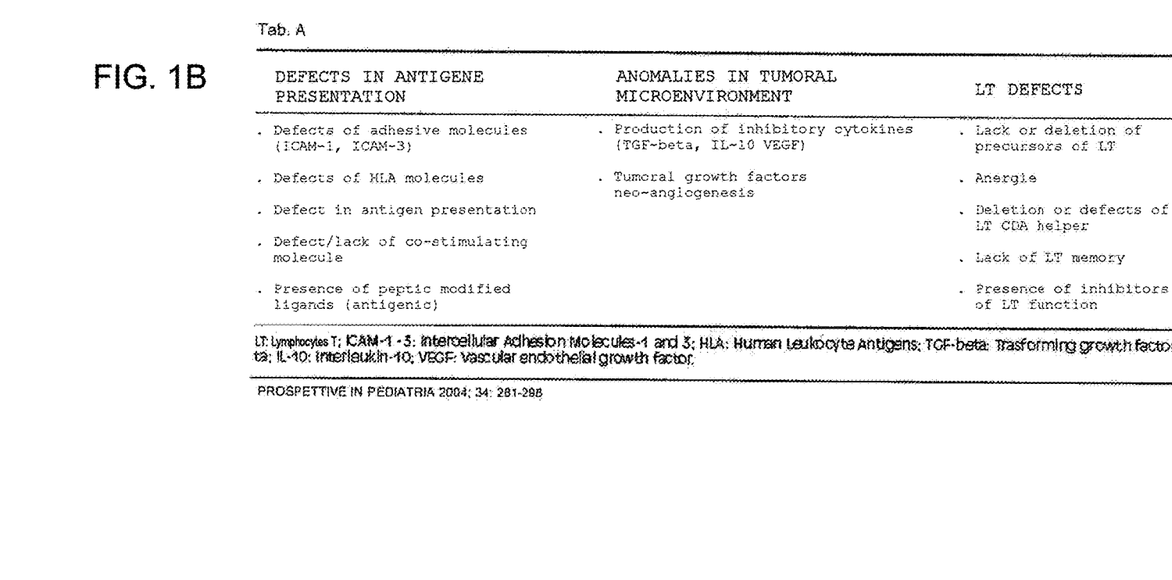

The anticancer immune response develops through various steps (see Fig. 1A), which require the presence of specific cytokines and/or chemokines, support cells such as antigen-presenting cells and cell effectors capable of tumor target-specific attack, by recognition of the Ag that activates the effector functions. Nevertheless, in spite of the immune response, immune cells cannot eliminate all the tumor cells, as the latter use a number of "escape" mechanisms (see FIG. 1B).

This generates somewhat an immune tolerance against tumor growth. Such events have been addressed by considering a number of therapeutic approaches, in which cell effectors are enhanced for more effective and persistent activity.

The most common therapeutic approaches include anti-cancer vaccination, adoptive cell immunotherapy and gene therapy.

In the first approach, cell effectors are caused to contact tumor-specific antigens and trigger response therefrom.

In adoptive immunotherapy, cell effectors are infused, after ex-vivo multiplication and purification thereof according to a selective anti-tumor activity.

Finally, gene therapy allows modification of cell effectors for more specific antigen recognition, followed by an enhanced and possibly more persistent anti-tumor response.

Figure 1C:
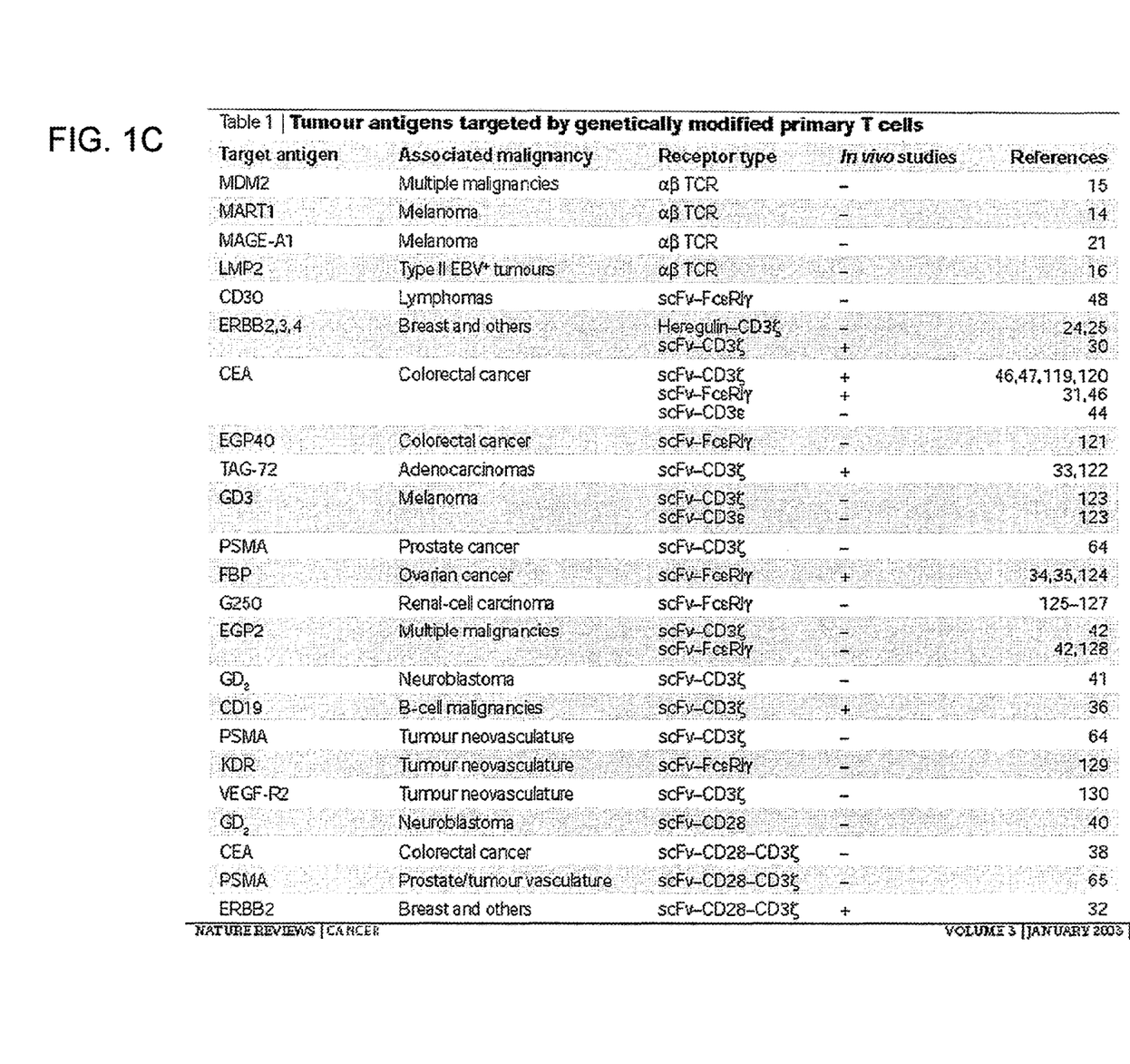

Such gene therapy has been tested for effectiveness against diseases such as melanoma, intestinal carcinoma, lymphoma, prostate cancer, kidney tumor, and even in acute and chronic lymphatic leukemia (FIG. 1C). These encouraging results suggested us to study a gene therapy approach using immune cells, that focused on tumor lines expressing a particular antigen, known as $G_{D2}$, on their cell membrane.

Gene Therapy with Anti-$G_{D2}$ Chemical Receptor-Expressing Immune Cells.

Disialoganglioside $G_{D2}$ is a ubiquitous molecule of the plasma membrane of neuroectodermal cells, which has a role in cell growth and differentiation, as well as the maintenance of cell-matrix adhesion.

Il $G_{D2}$ has been extensively investigated for the last 30 years, as it was found to be an interesting surface epitope characterizing various types of tumors of ectodermal and mesodermal origin.

Particularly, it is over-expressed by most of neuroblastoma (NB) and melanoma cells, and is absent or expressed at low levels in normal tissues.

In pediatrics, neuroblastoma, hereinafter shortly referred to as NB, is one of the most intensively studied tumors, as it has a yearly incidence of 7-10 cases/million, and ranks third in incidence among pediatric malignancies after leukemia and central nervous system tumors.

While the survival rate for low- and medium-risk NB cases has been ascertained, prognosis for high-risk NB cases is still low (<15%). Although the various therapies against NB have increased initial response rates, it is still difficult to achieve long-lasting remission in patients with disseminated disease.

Recent immunotherapy trials against NB showed susceptibility thereof to the action of effector cells, and suggest these procedures as a new interesting therapeutic approach to support existing therapies, with the purpose of preventing recurrence and ensuring long-term disease control.

Based on these trials, a number of therapeutic strategies for enhancing cell effectors have been implemented for NB treatment.

The first immunotherapy approaches consisted in infusing patients with tumor-specific anti-$G_{D2}$ monoclonal antibodies (MoAb in short), immune-modulating cytokines such as IL-2 and ex-vivo activated immune cells, as described for adoptive immunotherapy.

Concerning MoAbs, once the specific tumor antigen has been recognized, they can act at multiple levels, namely on the one hand by triggering a block by direct action, if the antigen is a functional receptor and on the other with an indirect action, through an Ab-dependent cytotoxicity process (ADCC), involving activation of cell effectors.

Furthermore, MoAbs have been conjugated with radioactive molecules, chemotherapeutic drugs or toxins, thereby acting as carriers for highly specific delivery of the active compound to the tumor site.

Figure 1D:
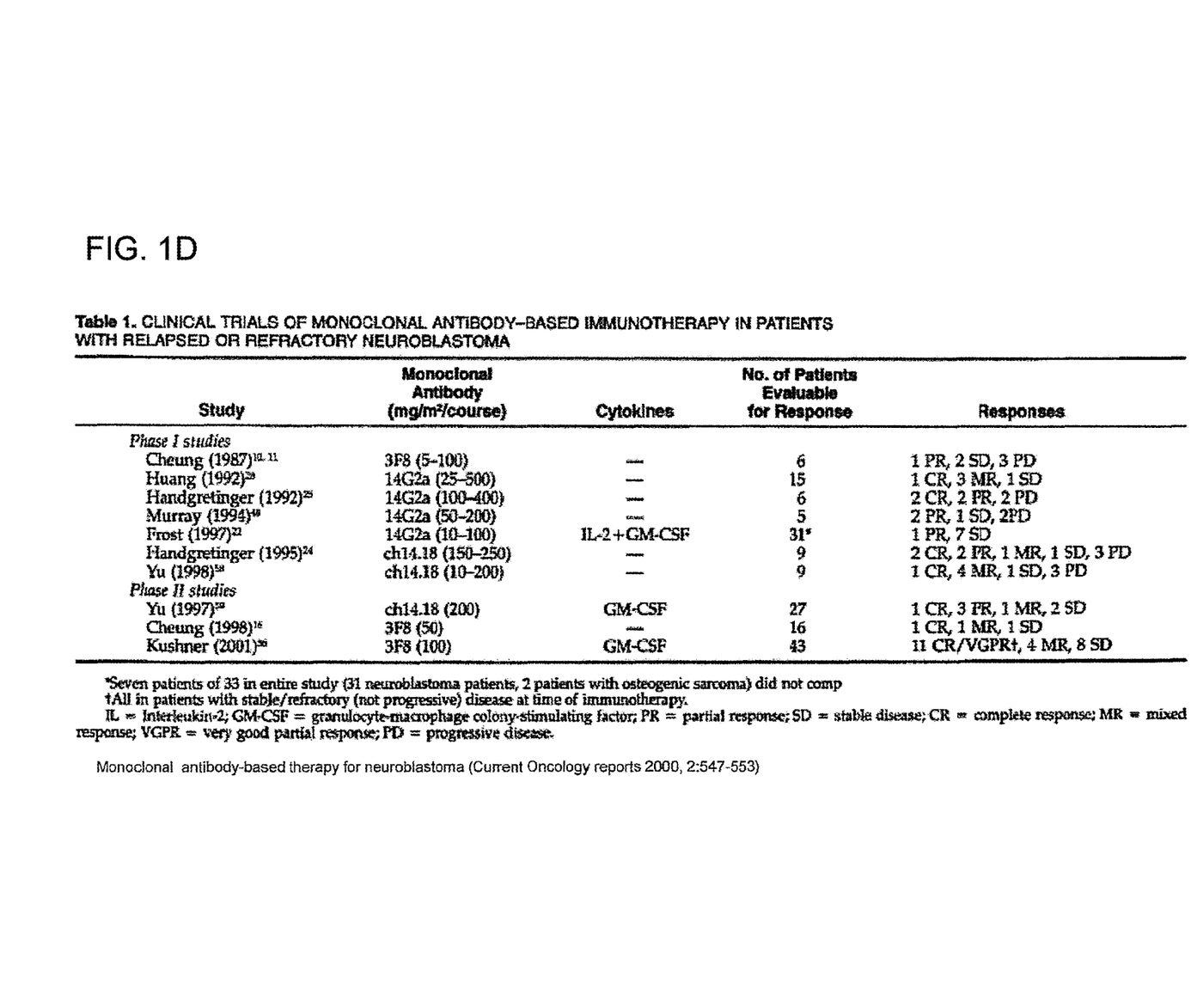

Also concerning NB, various clinical trials have been undertaken with anti-$G_{D2}$ MoAbs (see Fig. 1D) to trigger an immune response, although the first results that have obtained have shown poor success in NB recurrence treatment as well as high toxicity.

In order to obviate these limits, adoptive cell immunotherapy has been undertaken, using disialoganglioside $G_{D2}$ as a target antigen.

Immune cells have been modified for recognition and elimination of $G_{D2}$-positive tumors, thereby providing new therapeutic hopes not only to children affected by this tumor, but also to patients with tumors associated with high $G_{D2}$-antigen expression, such as: small cell lung carcinoma, melanoma and other tumors.

In 1 998, a New York-based team led by Sadelain M, noted that most tumor cells use an "escape" mechanism that consists in reduced presentation of molecules involved in co-stimulation to activation of the immune system, such as B7-1 and B7-2.

These molecules are required by the effector cells both for completing tumor cell recognition and for maintaining the established proliferative stimulus. Based on this assumption, a decision was made of modifying the T cells by providing them with a CR that is capable of recognizing $G_{D2}$-positive cells, and consists of the scFv of a $G_{D2}$-specific MoAb (3G6) associated with the co-stimulatory molecule CD28, which is required for effective activation of the anti-tumor action of lymphocytes.

The same chimeric receptor was produced in truncated form, i.e. lacking the intra-cytoplasmic portion, and was used as a control to validate the role of the CD28 molecule in the persistence of lymphocyte activation stimulus.

The first in vitro results showed that the CR 3G6-CD28 was not only able to allow specific recognition of $G_{D2}$-positive cells by T lymphocytes, but could also protect them from death induced by tumor microenvironment stimuli, thereby allowing selective expansion of modified lymphocytes, unlike the ECs expressing the truncated-form CR.

Although this study provided one of the first evidences of the important role of co-stimulatory molecules in ensuring proliferation and long-term survival of immune cells, it did not deal with the ability of modified lymphocytes to act against tumor cells, and did not assess their effectiveness in terms of anti-tumor immune action.

The team of Brenner M. K. and Rossig C, from the Baylor College of Medicine, Huston, conducted a study in 2001, in which T lymphocytes were genetically modified and used in NB treatment.

Here, CRs were generated whose intracytoplasmic domain had only the lymphocyte signaling molecule CD3ζ (with no co-stimulatory signal), fused with an extracytoplasmic domain composed of the scFv of the anti-$G_{D2}$ monoclonal antibody (sc14.G2a).

The T lynmphocytes obtained after transduction were able to stably express the CR with less than 30% efficiency, but this assessment, although not extended to all lymphocytes, ensured selective recognition and activation of such modified lymphocytes against $G_{D2}$-positive NB cells.

In spite of this, their function was found to decrease with time, when no appropriate co-stimulatory signal was provided, because antigen stimulation by the CR was not found to be able, alone, to adequately support cell proliferation.

These results support the feasibility of human T-lymphocytes redirection for treatment of an associated $G_{D2}$ tumor, but indicate that the success of CR-mediated adoptive immunotherapy requires additional strategies to support maintenance of EC activation.

More recent studies have shown that co-stimulatory molecules are required by immune cells not only to complete activation of the cytolytic action once the target (primary and secondary signals) is recognized, but to ensure such action with time.

These observations suggest that any gene modification of ECs presenting a CR in combination with a co-stimulatory signal may be a key to obtain specific and long-lasting immune responses.

These assumptions were used by Brenner M and his colleagues in 2008 to prove that cytotoxic T lymphocytes CD8+ (CTL) directed against tumor-associated non-viral antigens do not survive for a long time in the tumor microenvironment and show a limited in-vivo antitumor activity, whereupon the researchers decided to utilize their antiviral reactivity to make up for this limit.

Therefore, Epstein-Barr (EBV)-specific CTLs were genetically modified for expression of a CR directed against $G_{D2}$ and hence these genetically modified lymphocytes receive the co-stimulatory signal from their native receptors activated by the EBV virus, while the specific antitumor activity is mediated by the CR.

This study conducted on NB patients showed that EBV-specific CTLs expressing the anti-$G_{D2}$ CR survive for a longer time as compared both with the same CR-modified lymphocytes with no EBV specificity, and with CTLs having an anti-$G_{D2}$ CR, that has the CD3ζ chain as the only intra-cytoplasmic stimulatory signal.

The infusion of EBV-specific CTLs modified with the anti-$G_{D2}$ CR was found to be safe and was associated with tumor regression in one half of the tested individuals, which suggests it as an interesting adoptive cell immunotherapy approach, although in this case co-stimulation is not supported by an inherent property of the CR but by prior sensitization of ECs by the EB virus, which limits the field of action to individuals that had specific contact with such virus. Furthermore, individuals formerly exposed to the virus might have the virus in their T cells, as a condition that predisposes per se to development of lymphoid neoplasia.

Therefore, various co-stimulatory molecules have been studied and investigated through the years, for association to the CR and enhancement of its effectiveness. A remarkable molecule of this type is the 4-1 BB molecule, also known as CD137, and member of the TNF receptor family, which is essential for the antitumor activity of T cells.

In 2009, Campana D. et al. issued a study in which T lymphocytes were modified with an anti-CD19 CR (an important marker for acute lymphatic leukemia), which presented the 4-1 BB co-stimulatory molecule signaling domain at intra-cytoplasmic level.

The T lymphocytes genetically modified to express this CR have shown a potent and specific cytolytic activity against CD19-positive leukemia cells and such effectiveness was found to be better than that of lymphocytes modified with the same CR, lacking the 4-1 BB portion. Based on this and other previous studies, Campana D. et al. disclosed in patent application publication US2005/0113564 concerning "Chimeric receptors with 4-1 BB stimulatory signaling domain", the possibility of genetically modifying ECs by providing them with specific anti-CD-19 CRs having a highly efficient co-stimulatory molecule, thereby optimizing the activation and maintenance of the antitumor cytolytic stimulus with time.

All these studies provide the knowledge that treatments with large numbers of genetically modified effector cells may be used in clinical practice, due to their low hazard level, although successful use of this therapy may be hindered by low long-term persistence of these cells, as well as by an advanced state of the tumor disease.

Such data suggest the need of improving the immunologic action after transplantation by modifying the receptor structure to optimize its ability of both first activating the antitumor cytolytic process; and allowing a more effective long-time persistence of the effector cells at the tumor site, for real, long-term remission of the disease.

DISCLOSURE OF THE INVENTION

It is an object of the invention to improve the prior art.

Another object of the invention is to provide an anti-$G_{D2}$ cell, known as chimeric receptor, that is capable of high-affinity recognition of the disialoganglioside ($G_{D2}$) expressed at high levels in many human tumors of neuroectodermal origin, and absent or expressed at low levels in normal tissues.

Another object of the invention is to provide the anti-$G_{D2}$ chimeric receptor with a portion containing the 4-1 BB co-stimulatory molecule, thereby creating two distinct mutually fused portions: an intra-cytoplasmic portion and an extra-cytoplasmic portion. Such composite molecule, known as anti-$G_{D2}$-BB-ζ has a key role in the antitumor activity of the cell.

A further object of the invention is to provide an anti-$G_{D2}$-BB-ζ CR molecule to effector cells, for them to activate a cytotoxic action against $G_{D2}$-expressing cells.

Yet another object of the invention is to provide a method for in vivo production of ECs having a highly specific anti-$G_{D2}$-BB-ζ receptor that supports antitumor therapies.

In one aspect, the invention relates to a modified effector cell, also known as chimeric receptor, for treatment of anti-$G_{D2}$-BB-ζ-expressing tumors, to treat the $G_{D2}$-positive tumor, as defined hereinafter.

In a further aspect, the invention relates to a method of producing a modified effector cell for treatment of disialoganglioside $G_{D2}$-expressing tumors as defined in the features that are described hereinafter.

The method of producing the modified anti-$G_{D2}$-BB-ζ effector cell (or chimeric receptor) and the effector cell itself provide the following advantages:

providing a cell population having a phenotype that can be associated with an effector cell;

having the cell population associated with the effector cell express an anti-$G_{D2}$-BB-ζ molecule, known as chimeric receptor, to obtain a specific antitumor action against disialoganglioside $G_{D2}$-expressing cells;

acting as a support therapy for existing treatments, to prevent recurrence and ensure long-time disease control.

Unlike the existing formulations for creating an anti-$G_{D2}$ CR, the anti-$G_{D2}$-BB-ζ receptor of the present invention is composed of the two following portions: an extra-cytoplasmic portion, consisting of the scFv region deriving from the anti-$G_{D2}$ MoAb IgM (clone 126), capable of high-efficiency recognition of a disialoganglioside ($G_{D2}$) and an intra-cytoplasmic portion, consisting of the trans-membrane region of the lymphocyte molecule CD8a; a 4-1 BB molecule co-stimulation domain and a CD3ζ molecule activation domain as shown in FIG. 1.

Therefore, the invention achieves the following advantages:

a high binding affinity for the tumor antigen, due to the inherent property of the scFV region of the anti-$G_{D2}$ CR antibody;

immediate activation of the antitumor effector functions of the cells modified with the anti-$G_{D2}$-BB-ζ after antigen binding;

maintenance of this antitumor effect due to the persistence of the stimulus associated with the coexistence of the 4-1 BB co-stimulatory molecule in the structure of the CR;

the possibility of providing an adequate antitumor action with low effector cell-to-tumor cell ratios, thereby achieving eradication of tumor cells with smaller numbers of effector cells;

the possibility of modifying various types of cell effectors by activating or increasing a selective antitumor action thereof for the $G_{D2}$ antigen, due to the use of vectors that modify a large spectrum of eukaryotic cells.

BRIEF DESCRIPTION OF THE DRAWINGS

Further features and advantages of the invention will result more clearly from the description of a modified effector cell (also known as chimeric receptor) for treatment of anti-$G_{D2}$-BB-ζ tumors, which is stably provided to effector cells for treatment of abnormal $G_{D2}$-expressing cells, which is described by way of illustration and without limitation in the following description and with reference to the annexed figures, in which:

The construct portion encoding for the extracytoplasmic region of the CR is composed of:

a signal peptide containing an intron sequence;

the sequence encoding for the variable region of the light chain of the anti-$G_{D2}$ IgM antibody (clone 126);

a linker of 18 amino acids that allow proper folding of the $G_{D2}$ antigen recognition region;

the sequence encoding for the variable region of the heavy chain of the anti-$G_{D2}$ IgM antibody (clone 126);

The construct portion encoding for the transmembrane region and the intracellular region of the desired anti-$G_{D2}$-BB-ζ CR molecule is composed of:

the transmembrane region of the TRC receptor of cytotoxic T cells (CD8+);

the intracellular portion of the 4-1 BB co-stimulatory molecule (CD137);

the intracellular portion of the human lymphocyte CD3ζ molecule.

FIG. 5 is a schematic representation of the technique of separation of the anti-$G_{D2}$-BB-ζ CR-expressing modified effector cells. The CR is recognized by anti-idiotypic antibodies, obtained by immunization of BALB/c mice using the Gene Gun method. After immunization, the mice developed anti-idiotypic antibodies that recognize the scFv (extra-cytoplasmic) region of the anti-$G_{D2}$-BB-ζ CR. A second antibody (IgG) of different animal origin (rat), conjugated with immunomagnetic beads, can recognize and bind with the anti-idiotypic antibody. This system has been used to purify, by magnetic separation, the population of efficiently transduced effector cells, which express the anti-$G_{D2}$-BB-$\zeta$ CR, from those that have not been transduced.

DETAILED DESCRIPTION OF A PREFERRED EMBODIMENT

According to the invention gene therapy and adoptive immunotherapy have been combined to provide a therapeutic strategy that involves gene modification of previously ex-vivo expanded effectors by providing them with surface molecules, known as receptors, which can recognize tumor antigens and activate a specific cytolytic activity against them.

Gene Therapy with Chemical Receptor-Expressing Effector Cells.

This approach consists in gene modification of effector cells using gene sequences, known as "vectors" that can induce the expression of surface molecules, known as chimeric receptors (CR). The CRs are transmembrane structures composed of an intra-cytoplasmic component and an extra-cytoplasmic component which acts as an "anchor" and can recognize and specifically bind the tumor antigen of interest. The extra-cytoplasmic region, which is responsible for recognition of the tumor Ag, consists of a variable fragment (scFv) of murine Ag-specific immunoglobulins (Ig), whereas the intra-cytoplasmic region consists of parts of molecules of human origin, which are responsible for immune response activation. The junction of these two basic functions provides a new molecule, defined as a chimeric molecule, that has the advantage of high specificity and efficiency and by-passes tumor escape mechanisms. Once the binding of the chimeric receptor and the specific antigen has taken place, the CR transmits the activation signal into the effector cell, thereby triggering the immune response in direct, highly specific fashion.

Creation of the Anti-$G_{D2}$-BB-$\zeta$ CR.

The construct (DNA chain) encoding for the anti-$G_{D2}$-BB-$\zeta$ CR is basically composed of two portions: an extra-cytoplasmic component that can specifically recognize the antigen sequence of interest (disialoganglioside $G_{D2}$) and an intra-cytoplasmic component that can effectively transmit the effector cell activation signal.

Then, the sequences of the two portions of the molecule known as anti-$G_{D2}$-BB-$\zeta$ CR were assembled by the technique known in the art as PCR Splicing by Overlap Extension (SOE-PCR). The cDNA encoding for the scFv region of the anti-$G_{D2}$ monoclonal IgM, derived from hybridoma 126, was obtained by amplification of this region of the pcDNA3-$G_{D2}$-h$\epsilon$SIP molecule.

On the other hand, the intra-cytoplasmic region is composed of various parts, including: the transmembrane portion of the TRC receptor of cytotoxic T lymphocytes (CD8a); the intracellular portion of the 4-1 BB co-stimulatory molecule and the intracellular activating portion of the lymphocyte O'O3-$\zeta$ molecules, which form together the "Signal Transduction Machinery (STM)".

The two components of such chimeric receptor were assembled by using the Splicing by Overlap extension (SOE-PCR) technique. Such process provided the construct encoding for the anti-$G_{D2}$-BB-$\zeta$ CR. A truncated form of this CR was also generated. Such truncated form lacks the intra-cytoplasmic region comprising the 4-1 BB e CD3-$\zeta$ molecules and only has the transmembrane portion of the CD8 molecule of the TRC of the cytotoxic T lymphocytes (CD8$\alpha$).

Figure 2A:
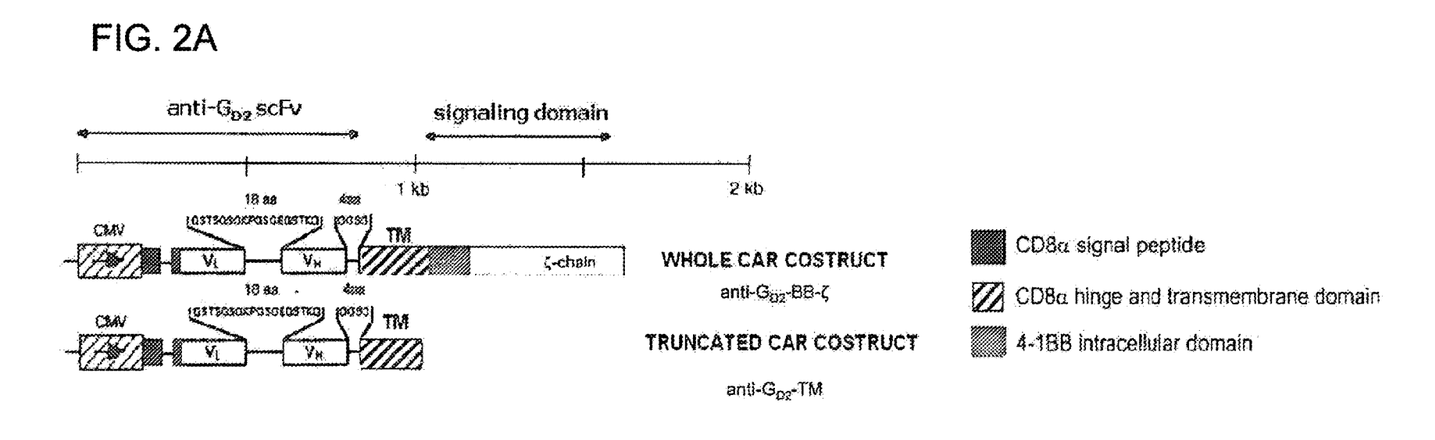
FIG. 2A is a detailed representation of the various functional domains of the construct encoding for the anti-$G_{D2}$-BB-ζ chimeric receptor (and its anti-$G_{D2}$-TM truncated version) where.
Figure 2B:
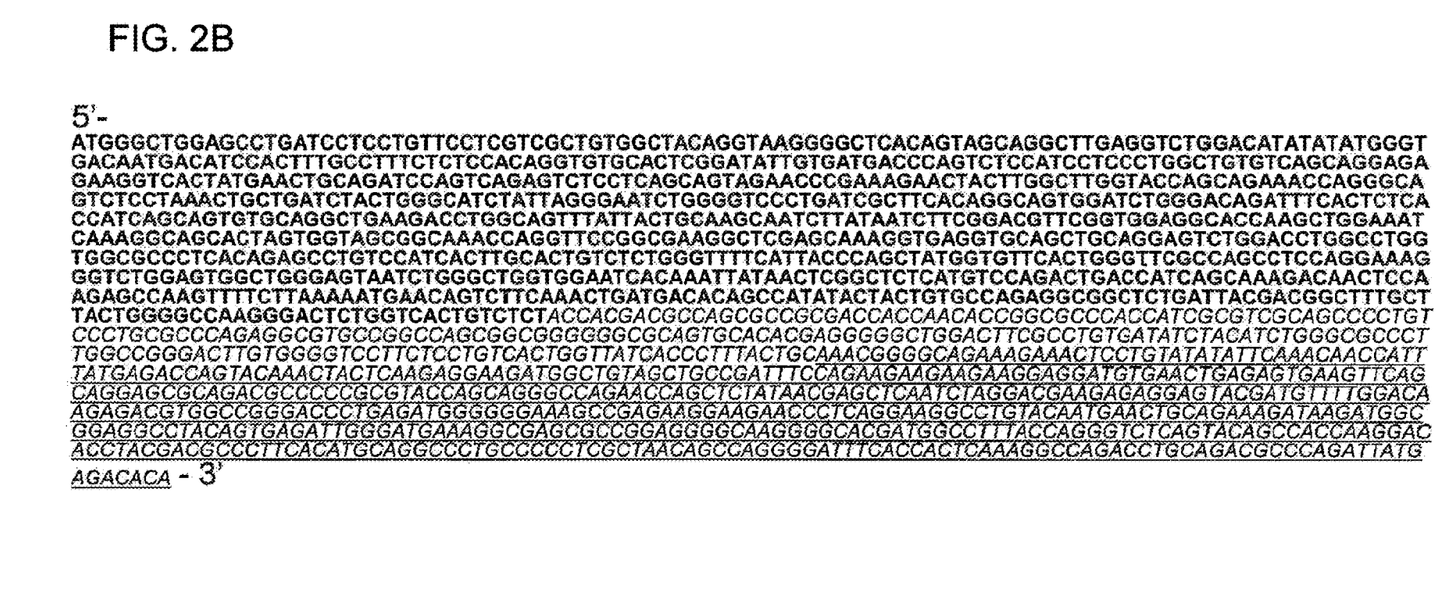
FIG. 2B is a DNA sequence encoding for the molecule known as anti-$G_{D2}$-BB-ζ chimeric receptor in its full-length form, composed of 1612 base pairs. The scFv portion is in bold text, the STM is in italics. The truncated form of the CR, known as anti-$G_{D2}$-TM CR, which lacks the intracytoplasmic activation domain, indicated in underlined text, is composed of a DNA sequence having a full length of 1087 base pairs.
Figure 3:
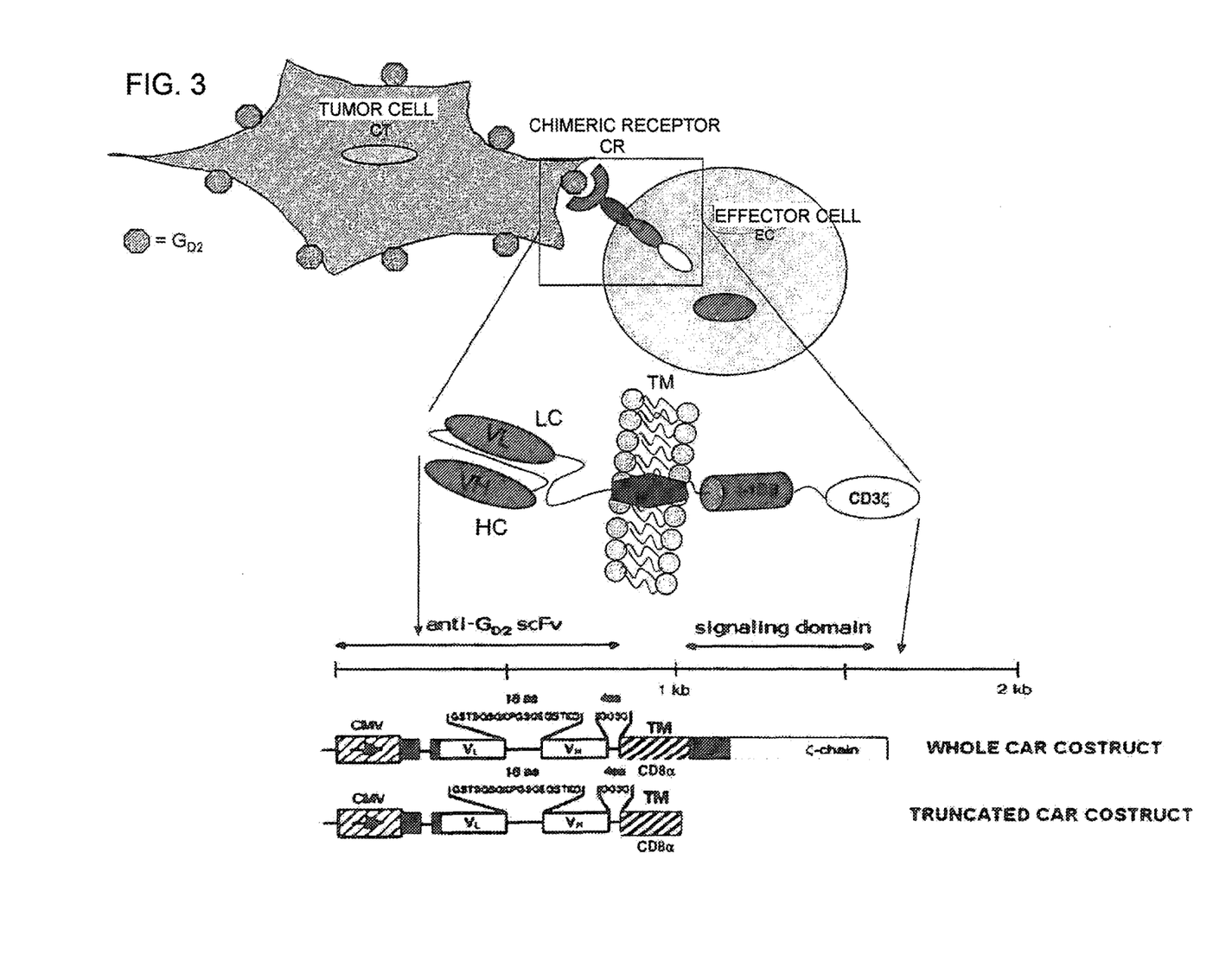
FIG. 3 is a schematic representation of the invention, showing that the previously described sequence encodes for a CR characterized by an extra-cytoplasmic region, a transmembrane region and an intra-cytoplasmic region. The extra-cytoplasmic region is required for $G_{D2}$ antigen recognition on the surface of target tumor cells; the intra-cytoplasmic region has the role of activating and maintaining the cytolytic stimulus of the effector cells upon bonding with the $G_{D2}$ antigen; the transmembrane region binds these two portions and allows proper localization thereof on the cell membrane.

The truncated form of the CR, known as anti-$G_{D2}$TM CR, was generated by amplifying the DNA of the construct encoding for the anti-$G_{D2}$-BB-$\zeta$ CR, but using a different reverse primer (5'-GCCTTAAGGCTTAGCAG-TAAAGGGTGATAACCAGTGACAG-3') that contains a restriction site for the EcoRI enzyme in its 5' region. The construct so formed is shown in FIG. 2A, whereas the full-length DNA sequence encoding for the CR is described in FIG. 2B.

Generation of the Viral Vector to Create the Anti-$G_{D2}$ CR-Expressing Effector Cell.

A population of carrier cells that can stably produce a pool of retroviral particles capable of infecting the effector cell population of interest, was created through two steps.

The first step based on the obtainment of a cell line producing the retrovirus in transient mode and the second step aimed at obtaining the generation of a Producer Cell Line (PCL) capable of stably producing a retroviral progeny. For the transient step, embryonic renal fibroblasts (293 T cells), held at about 70% confluence, were transfected with a solution of 5 µg (in a 25 cm$^2$ flask) total plasmid DNA and with the help of polycations.

Later, the retroviral supernatant obtained by transient transfection of 293T was collected and used to infect the PLC deriving from a human fibrosarcoma line; 24 h after infection the cells were analyzed by cytofluorimetry to check positivity of green fluorescent protein (GFP), an infection efficiency marker.

The viral supernatant collected from the PCLs, was used to infect the effector cells.

Transformation of Effector Cells.

The effector cells (hereinafter shortly referred to as ECs) were separated from the rest of the peripheral blood cell components, by density gradient centrifugation (Ficoll) and were later pre-stimulated for 48 hours with Interleukin 2 (IL-2) and phytoematoagglutinin (PHA-M), as retroviruses only exhibit a high infecting power in the cells during active replication.

The ECs, adhered to a plastic support using retronecting, were submitted to three infection hits, each 24 h, with the viral supernatant obtained from the PCLs and later showed a strong CR surface expression ability (48% average infection efficiency).

This process was also carried out to produce ECs expressing the CR in its truncated form; therefore, three types of modified ECs were created:

ECs transduced with the empty vector, known as "EC-CN" (not recognizing $G_{D2}$ but expressing the GFP);

ECs expressing the anti-$G_{D2}$TM CR (recognizing $G_{D2}$ but not reacting against cells having such antigen);

ECs expressing the anti-$G_{D2}$-BB-ζ CR, (capable of both recognizing $G_{D2}$-positive cells, and having a cytocidal action thereagainst).

Figure 4:
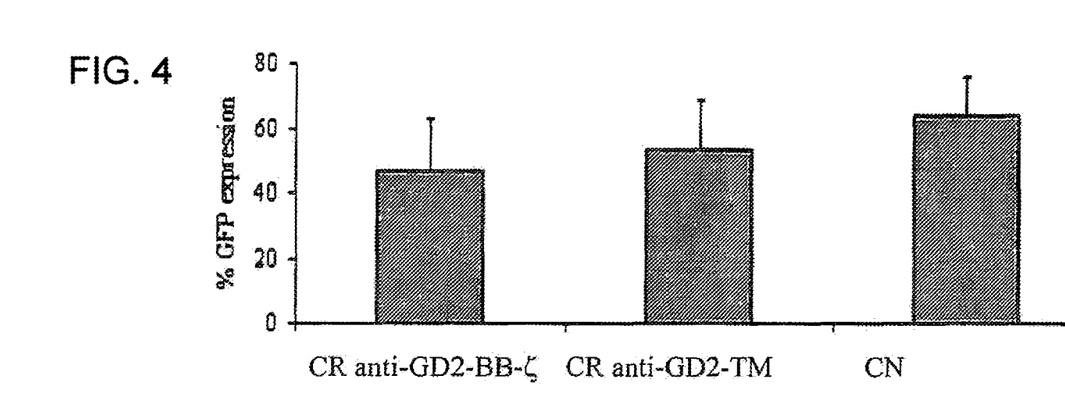
FIG. 4 is an analysis of the efficiency of transduction of the ECs with the three different constructs, by assessment of the amount of fluorescence emitted by the green fluorescent protein marker (GEP) encoded by the vector we used. The constructs encode for the (full-length) anti-$G_{D2}$-BB-ζ CR; the (truncated) anti-$G_{D2}$-TM CR respectively; in addition a construct is provided which does not express the CR, known as an empty vector, that only expresses the GFP protein, and is used as a control (CN).

At the end of the transduction step, the ECs were left in their standard medium for a few days before cytofluorimetric analysis to check for expression of the GFP protein marker (FIG. 4) and later of the CR on the cell surface.

The CR expression was determined by sequential use of two antibodies. The first is an anti-idiotypic antibody of murine origin that can recognize the extra-cytoplasmic region of the CR (particularly the variable fraction of the anti-$G_{D2}$ antibody).

Then, rat polyclonal fluorochrome-marked antibodies where used, capable of being associated with the anti-CR IgG antibodies and allowing cytofluorimetry analysis.

Such anti-idiotype was obtained by immunization of BALB/C mice that received gold particles having a part of the CR-encoding DNA previously attached thereto, at skin level, by gene gun delivery.

The gold particles promote development of a local immune reaction mediated by skin dendritic cells, which phagocytize these particles and process the DNA attached thereto, to "lend" them to the B-lymphocytes that activate a specific antibody response. The immunized mice produced relatively large amounts of anti-idiotypic polyclonal antibodies in the serum, that could recognize the scFv portion of the CR expressed on the ECs.

Purification of the Membrane Chimeric Receptor-Expressing Lymphocyte Population by an Immunomagnetic Method.

In order to implement purity of the chemical receptor-expressing EC population, and hence to exceed the 50% threshold, averagely obtained by infection thereof by retroviruses, a method was used of separating the transformed cells from the remaining cell population.

The chimeric cell population is separated from the total population using MACS LD columns for immunomagnetic depletion sorting.

The operation includes marking of CR-expressing ECs with a primary antibody, which is later recognized by a secondary antibody bonded to a ball, which is retained in the column by a magnetic charge.

Figure 5:
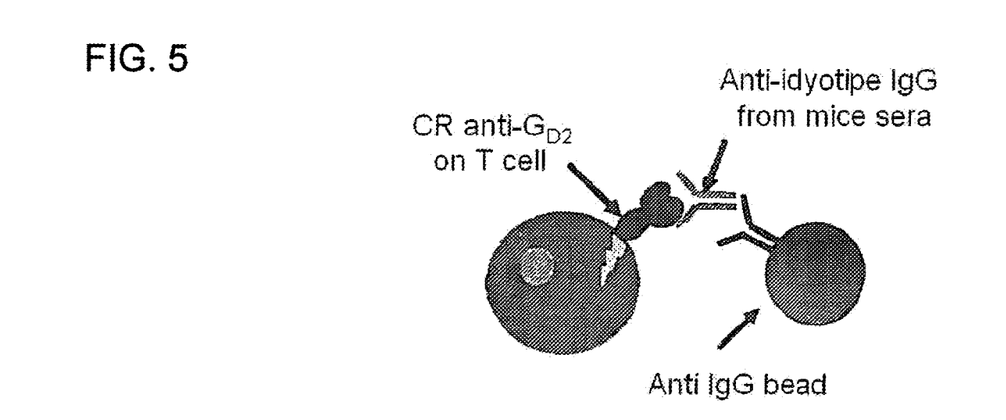

The bond thus obtained is given by the CR on the ECs with a (mouse anti-human) anti-idiotypic antibody, and a final antibody conjugated with the immunomagnetic balls (rat anti-mouse IgG1 MicroBeads) which retain the modified cells in the column inserted in the magnetic support, whereas unmodified cells move beyond the length of the column and may be thus separated (FIG. 5).

Figure 6:
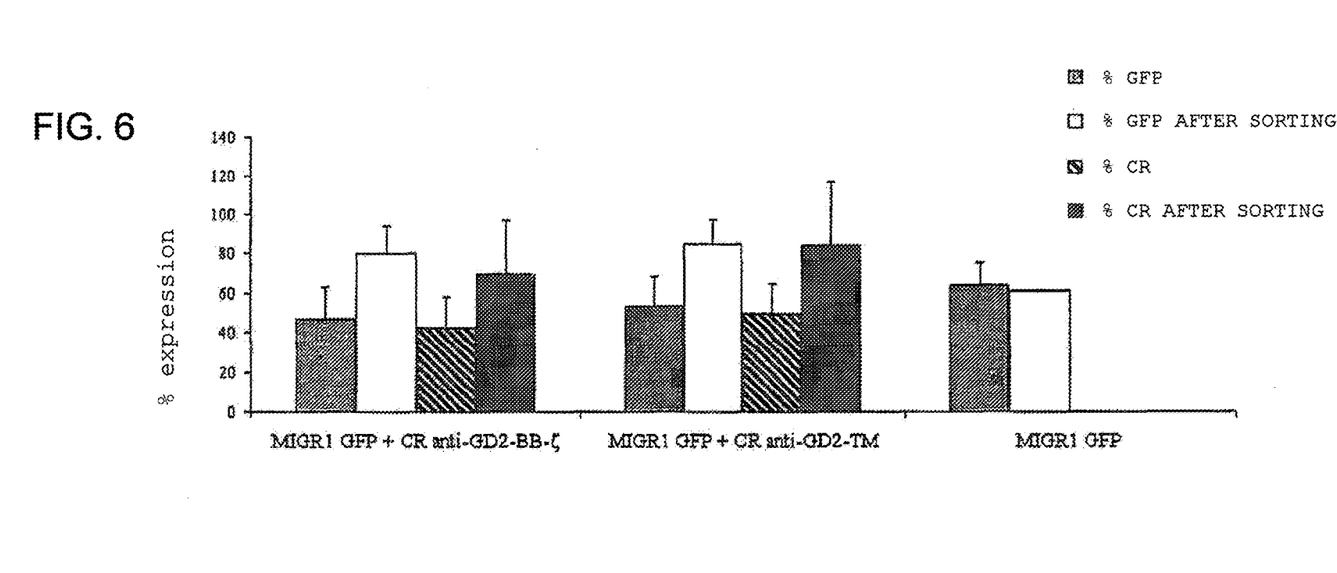
FIG. 6 is a representation of the efficiency with which the effector cells are infected by the various vectors before and after cell sorting/separation. The detection of the GFP protein marker indirectly indicates vector transduction efficiency (gray and white bars), whereas direct detection of the efficiency of CR transduction on the surface of effector cells is provided using the anti-idiotypic antibody, followed by an antibody conjugated with a fluorochrome (striped and black bars).
Figure 7:
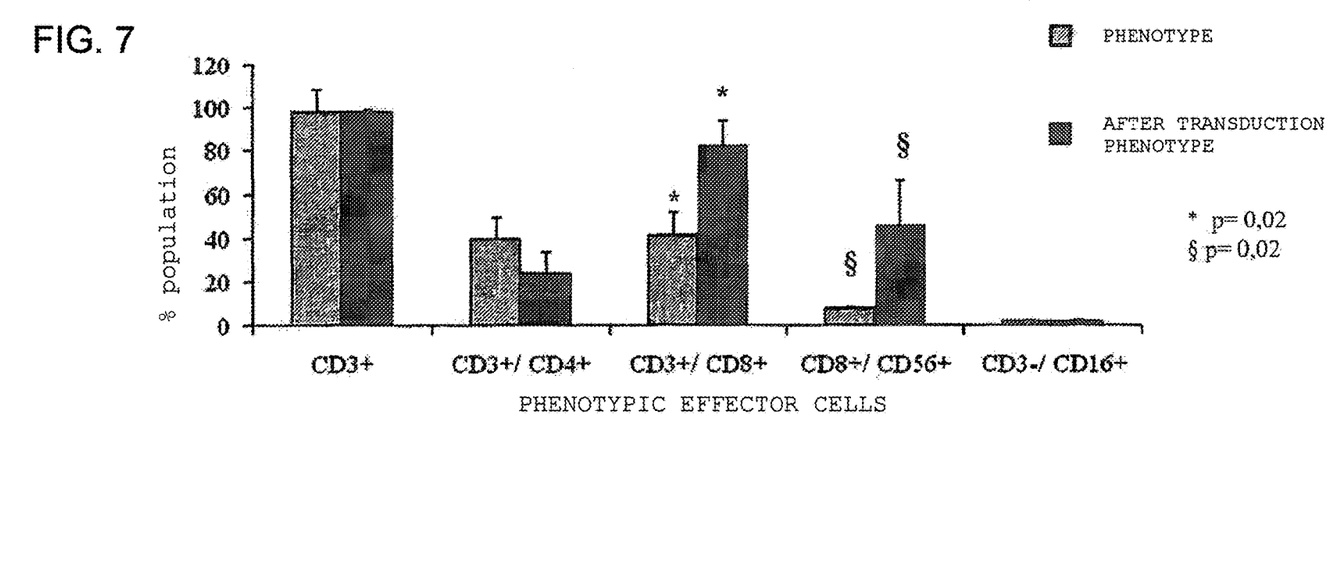
FIG. 7 shows data concerning the phenotypic characterization of the effector cells performed both after separation of such effector cells on the gradient of peripheral blood (day 0, gray bars) and after the transduction process, with the vectors encoding for CR (day 15, black bars).

By simply removing the column from the magnetic support, the CR-expressing ECs fall off, are collected and maintained in cell culture. This procedure can enrich the chimeric lymphocyte population from 50% to 70-80% (i.e. by about 20%) (FIG. 6).

Analysis of Disialoganglioside $G_{D2}$ Expression on Neuroblastoma Tumor Cells.

Figure 8:
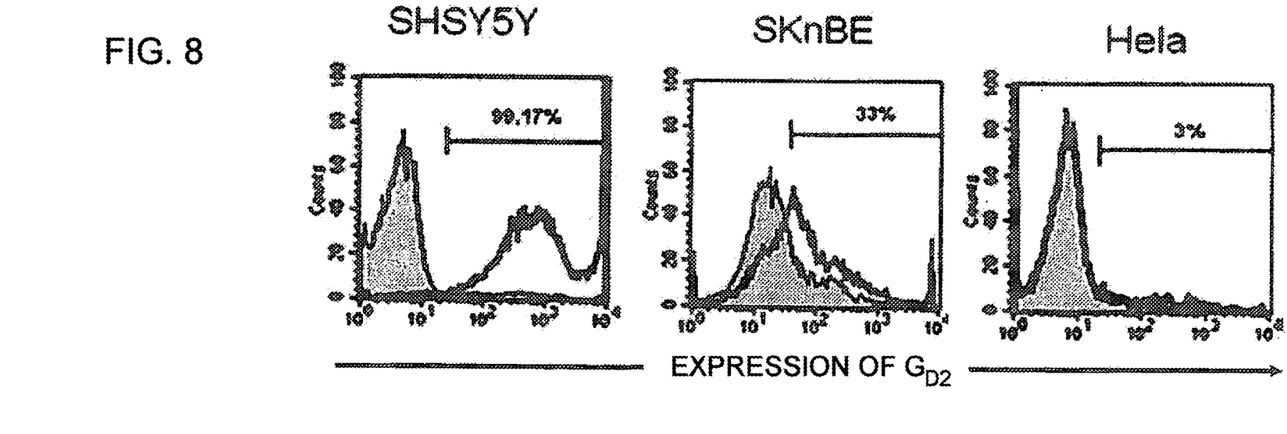
FIG. 8 shows a cytofluorimetry analysis characterization of the level of membrane expression of the $G_{D2}$ antigen by various tumor cell lines. Particularly, neuroblastoma cell lines (SH-SY-5Y, SKnBE) typically express disialoganglioside $G_{D2}$ on the membrane, whereas the cervix carcinoma cell line (Hela) does not express $G_{D2}$.
Figure 9:
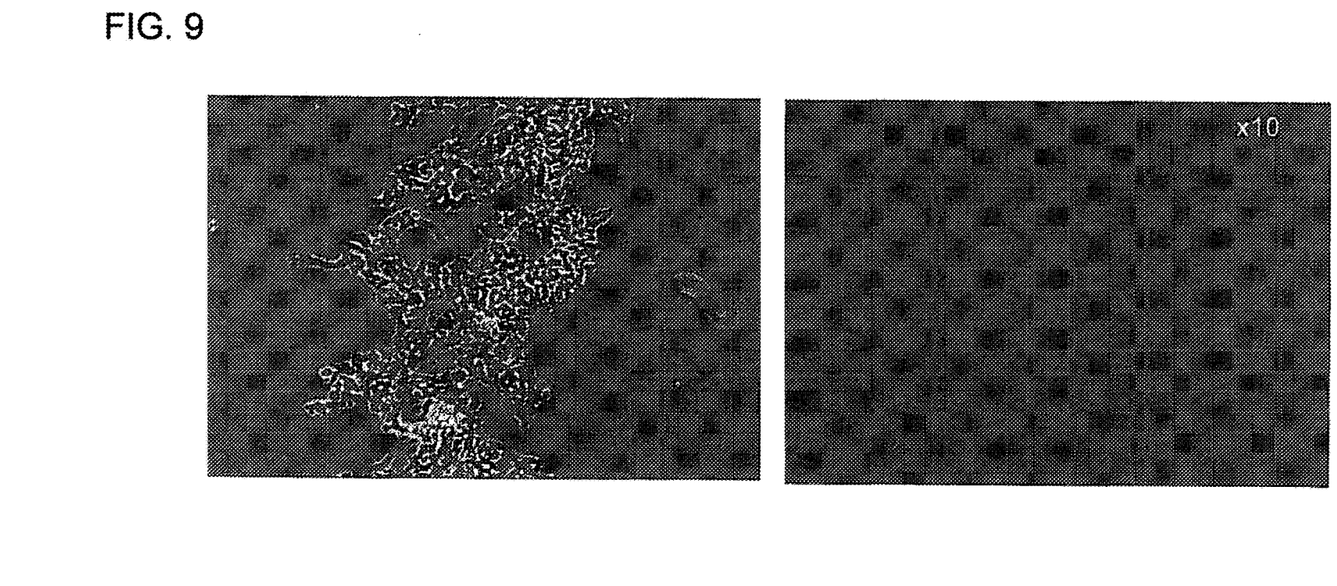
FIG. 9 is a detail of the disialoganglioside $G_{D2}$ expression on the surface of the SH-SY5Y neuroblastoma tumor line, analyzed by immunofluorescence using a fluorescence microscope (10× magnification). The following antibodies were used for such assessment: primary anti-$G_{D2}$ antibody (BD); secondary goat anti-mouse antibody, anti-mouse (all Ig classes) conjugated with rhodamine.

Two neuroblastoma tumor cell lines are available at the laboratory (FIG. 8):

SH-SY-5Y: clone isolated in 1970 from a 4 year-old girl (metastasized mass at bone level), $3^{rd}$ subclone obtained from the SK-N-SH neuroblastoma cell line.

SK-n-BE: clone isolated in 1972; a 2 year old boy with disseminated neuroblastoma (bone marrow biopsy) even after repeated chemotherapy cycles. The SK-N-BE (1) and (2) lines are obtained from the same patient but 5 months apart.

The human cervix carcinoma cell line (Hela), with no surface-expressed target antigen, was considered as a control target line.

Detection was carried out for the target $G_{D2}$ antigen by cytofluorometry. Namely, tumor cells were first contacted with an antibody capable of recognizing the membrane-expressed $G_{D2}$ antigen (Purified mouse anti-human disialoganglioside $G_{D2}$ monoclonal antibody—BD), followed by the addition of an antibody defined as secondary antibody, capable of fluorescence emission after bonding with the primary antibody (APC Goat Anti-Mouse Ig polyclonal—multiple adsorption, BD).

This analysis showed that all analyzed NB lines express relatively large amounts of $G_{D2}$ in their membrane, respectively 99% SH-SY5Y and 33% SK-n-BE, whereas the Hela cell line confirmed the assumed absence of $G_{D2}$ on the cell surface.

Therefore, the tumor lines being considered can be suggested as optimal targets for the kind of therapy involved in this invention.

Study of the Action of the Transformed Lymphocyte on Tumor Cell Lines and/or Primary Tumor Cells.

The last invention implementation step is characterized by the study of the action of genetically modified effector cells on tumor cell lines and/or primary tumor cells, through the development of a number of assays for assessment of cytotoxicity, specificity and proliferative abilities.

According to the invention, various laboratory studies have been conducted:

study of the action of modified ECs against tumor cell lines in a short-term (4 h) cytotoxicity assay;

study of the action of modified ECs against tumor cell lines in a long-term (6-day) cytotoxicity assay;

assessment of actual activation of modified ECs after short-term (24 h) contact with tumor cell lines.

1. Study of the Action of Modified ECs Against Tumor Cell Lines in a Short-Term (4 h) Cytotoxicity Assay.

This study is aimed at assessing the cytolytic action of the ECs against $G_{D2}$-positive tumor cell lines, by an in-vitro cytotoxicity assay with Chromium$^{51}$ ($Cr^{51}$) conducted 4 hours after co-culture.

The target cells were marked with an appropriate amount of $Cr^{51}$, and the effector cells were later added in the desired ratios.

The cell supernatant collected at the end of the 4 hours' co-culture contained free $Cr^{51}$ amounts directly related to the amount of the tumor cells lysed by the ECs.

The cell supernatants were analyzed using MicroBeta Trilux, and the percent release of specific $Cr^{51}$ was calculated using the appropriate formula.

Figure 10:
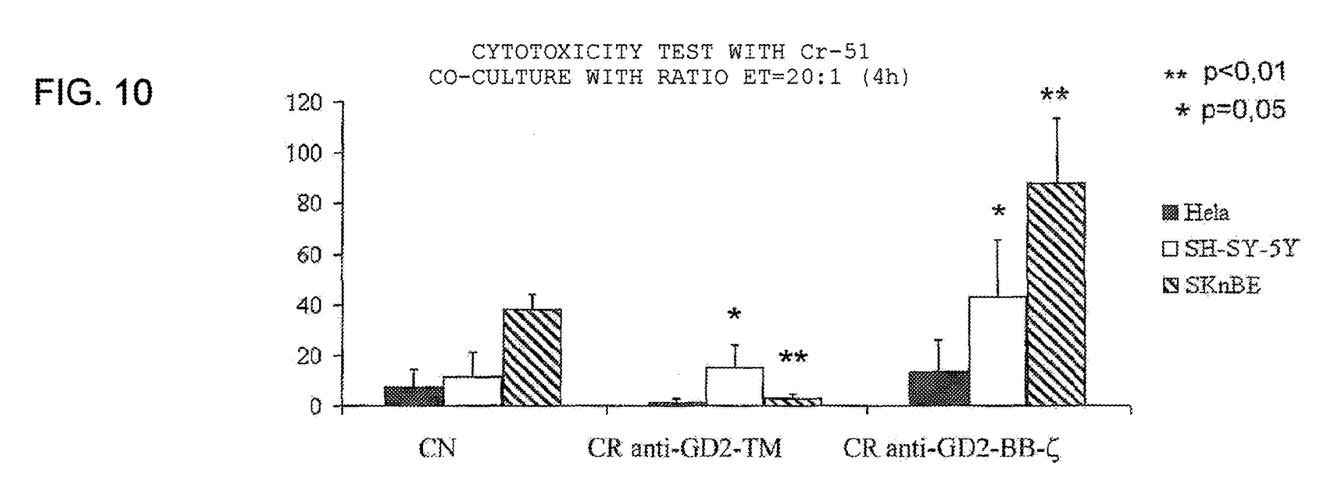
FIG. 10 is an analysis of the cytotoxic ability of effector cells with the anti-$G_{D2}$-BB-$\zeta$ chimeric receptor or the receptor in the anti-$G_{D2}$-TM truncated form, against tumor cell lines, as measured by the radioactive chromium$^{-51}$ release array, after 4 hours co-culture.

The data obtained by the $Cr^{51}$ assay shows a different cytotoxic activity of ECs with the anti-$G_{D2}$-BB-ζ CR as compared with those modified with the empty vector (CN), with respect of the SH-SY-5Y line, particularly after 4 h co-culture, with a Target cell: Effector cell (T:E) ratio of 1 to 20: the anti-$G_{D2}$-BB-ζ CR ECs showed a significant cytotoxic effect, i.e. 42.7%, against 11-7% obtained with the CN ECs (p=0.05) (FIG. 10).

Likewise, the cytotoxic reaction against the SKnBE line by the anti-$G_{D2}$-BB-ζ CR ECs as compared with those modified with the empty vector (CN), or with the truncated anti-$G_{D2}$-TM CR construct, proved to be highly specific and significant. The anti-$G_{D2}$-BB-ζ CR ECs exhibit a high short-time cytotoxic effect (88±25%) which is statistically significant when compared with the cytotoxic effect obtained with the other two types of effector cells; particularly having a significance p<0.01 when compared with the anti-$G_{D2}$-TM CR ECs; and a significance p=0.05 against CN ECs).

The lack of a cytotoxic effect of ECs against the $G_{D2}$-negative tumor cell (Hela) proves the high specificity of the cytolytic action of the ECs modified for expression of the anti-$G_{D2}$-BB-ζ CR.

Figure 11:
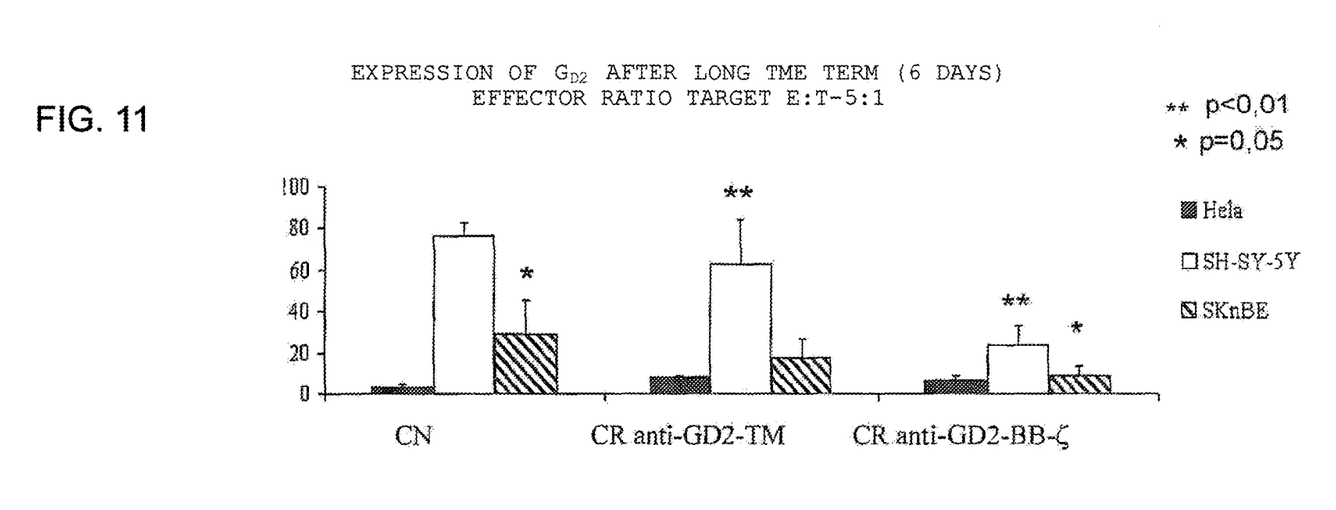
FIG. 11 is an assessment of the reduction of $G_{D2}$ positive tumor cells caused by the long-term (6-day) co-culture condition with modified effector cells.

2. To confirm such data, cell populations were characterized by cytofluorometry, at the end of 6-day co-cultures with a low E:T ratio=5:1. A significant decrease (from 92% to 23±9%, p<0.004) of $G_{D2}$ expression was noted on the surface of NB cells from the SH-SY-5Y line, in the presence of anti-$G_{D2}$-BB-ζ CR ECs; whereas with the ECs with the anti-$G_{D2}$-TM CR this percent remained almost unchanged (from 92% to 63.8±20%) (FIG. 1 1).

A significant reduction in $G_{D2}$ expression (from 37% to 9.02±4.4%) with anti-$G_{D2}$-BB-ζ CR ECs was also noted against the $G_{D2}$-positive SKnBE tumor line; conversely, with the CN control cells, this percent had no significant decrease (from 37% to 29.48±17%).

3. Study of the Activation of the Transformed Lymphocyte Against Tumor Cell Lines.

The activating response of effector cells is typically also characterized by up-regulation of the IL-2 receptor (CD25) on the cell surface.

This signal promotes cell proliferation, as well as cytokine production and secretion of cytolytic granules, with a consequent cytotoxic effect on target cells.

In order to compare the different abilities of the two CRs to induce antitumor responses, we analyzed these parameters in response to the interaction between the ECs and the $G_{D2}$-positive neuroblastoma lines.

Short-term EC activation was assessed after a 24 h co-culture by cytofluorometry. The ECs were differentiated from the target cell for their expression of the GFP protein.

Figure 12:
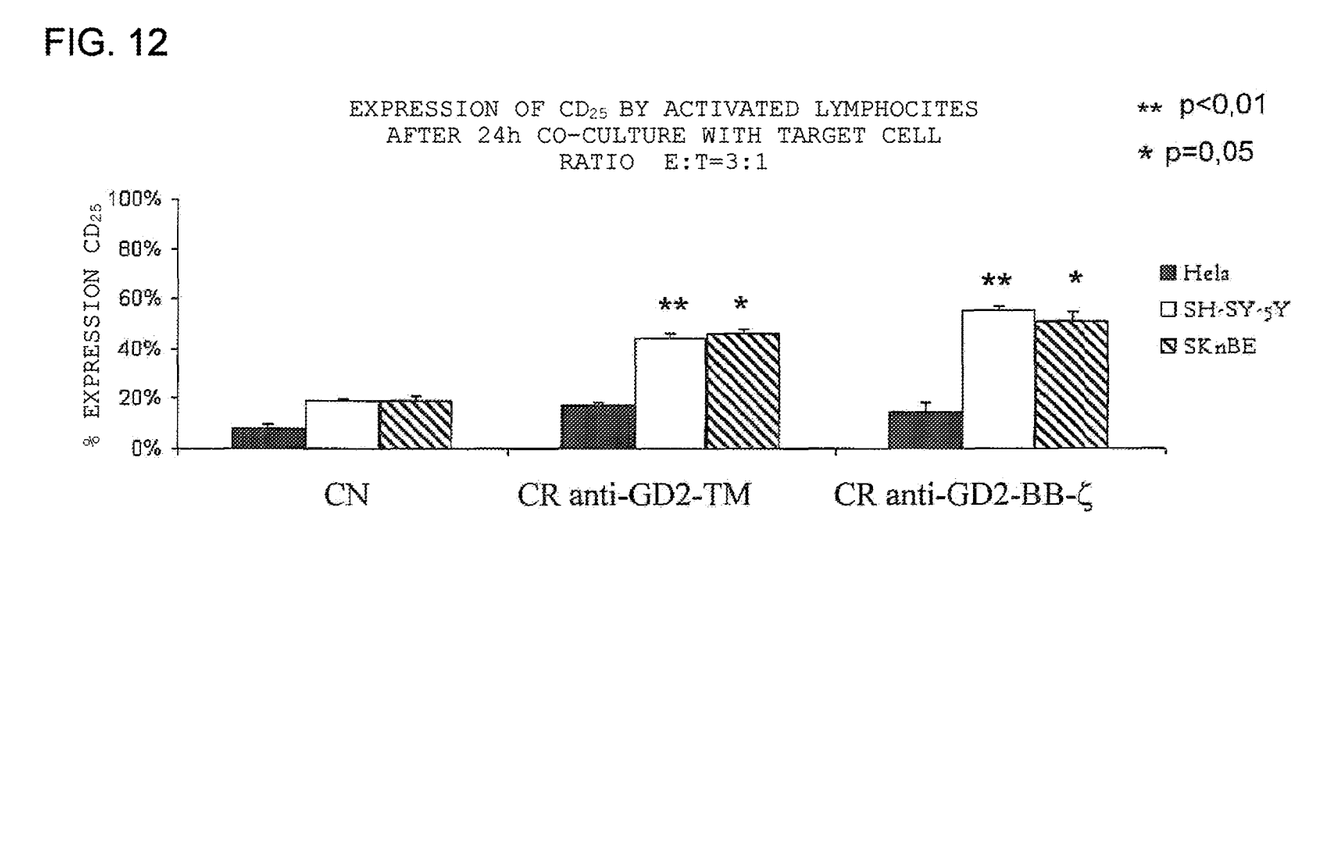
FIG. 12 is an assessment of the expression of the receptor molecule CD25 (Interleukin 2, IL-2 receptor) on the surface of effector cells active by tumor cell recognition.

After a 24 hours' co-culture with low E:T ratios (here E:T=3:1) we noted a significant up-regulation of the CD25 molecule on the surface of ECs with the anti-$G_{D2}$-BB-ζ CR as compared with both those modified with the anti-$G_{D2}$-TM CR, and with the CN ECs (FIG. 12).

Particularly, after a co-culture with SH-SY5Y cells, the ECs modified with the anti-$G_{D2}$-BB-ζ CR showed a high CD25 expression (55±1.3%) as compared with that detected with the anti-$G_{D2}$-TM CR (44±1.1%) and with the CN control cells (19.4±0.9%).

These differences are also statistically significant (p<0.01).

The same considerations apply concerning EC activation triggered by the $G_{D2}$-positive SKnBE tumor line, with no specific activation being found by the modified ECs against the $G_{D2}$-negative Hela tumor line, to confirm that the activation of these CRs allow specific selection of $G_{D2}$-positive tumor cells, with optimized cytolytic response by the effector cells modified with the anti-$G_{D2}$-BB-ζ CR.

The invention has been found to fulfill the intended objects.

The invention is susceptible to changes and variants within the inventive concept.

Furthermore, all the details may be replaced by other technically equivalent elements, as needed, without departure from the scope as defined by the following claims.

The invention claimed is:

1. A modified effector cell for treating disialoganglioside GD₂-expressing neoplasia, comprising:
   a cytoplasm with a nucleus therein, the cytoplasm being enclosed in a membrane; and
   a chimeric receptor, wherein the chimeric receptor comprises an extracytoplasmic portion, a transmembrane portion, and an intracytoplasmic portion,
   wherein the extracytoplasmic portion comprises, in order:
      a signal peptide containing an intron sequence,
      a first sequence encoding for a variable region of a light chain of the anti-GD₂ immunoglobulin M (IgM) antibody,
      a linker that allows folding of a GD₂ antigen recognition region of an anti-GD₂ IgM antibody, and
      a second sequence encoding for a variable region of a heavy chain of the anti-GD₂ IgM antibody, and
   wherein the transmembrane portion and the intracytoplasmic portion comprise, in order:
      a hinge and transmembrane domain of a human lymphocyte CD8α molecule,
      an intracellular portion of a 4-1BB co-stimulatory molecule, and
      an intracellular portion of a human lymphocyte CD3-ζ molecule.

2. The modified effector cell as claimed in claim 1, wherein the chimeric receptor is encoded by the sequence set forth in SEQ ID NO: 1.

3. The modified effector cell as claimed in claim 1, wherein the linker that allows folding of the GD₂ antigen recognition region consists of 18 amino acids.

4. The modified effector cell as claimed in claim 1, wherein the anti-GD₂ IgM antibody is from clone 126.

5. A polyclonal mixture of effector cells for treating disialoganglioside GD₂-expressing neoplasia, comprising:
   a plurality of modified effector cells comprising:
      a cytoplasm with a nucleus therein, the cytoplasm being enclosed in a membrane; and
      a chimeric receptor, wherein the chimeric receptor comprises an extracytoplasmic portion, a transmembrane portion, and an intracytoplasmic portion, wherein the extracytoplasmic portion comprises, in order:
a signal peptide containing an intron sequence,
a first sequence encoding for a variable region of a light chain of the anti-$GD_2$ immunoglobulin M (IgM) antibody,
a linker that allows folding of a $GD_2$ antigen recognition region of an anti-$GD_2$ IgM antibody, and
a second sequence encoding for a variable region of a heavy chain of the anti-$GD_2$ IgM antibody,
wherein the transmembrane portion and the intracytoplasmic portion comprise, in order:
a hinge and transmembrane domain of a human lymphocyte CD8α molecule,
an intracellular portion of a 4-1BB co-stimulatory molecule, and
an intracellular portion of a human lymphocyte CD3-ζ molecule, and
wherein at least 20% of the modified effector cells comprises a CD3+/CD8+/CD56+ phenotype.

6. The polyclonal mixture of effector cells as claimed in claim 5, wherein the chimeric receptor is encoded by the sequence set forth in SEQ ID NO: 1.

7. The polyclonal mixture of effector cells as claimed in claim 5, wherein the linker that allows folding of the $GD_2$ antigen recognition region consists of 18 amino acids.

8. The polyclonal mixture of effector cells as claimed in claim 5, wherein the anti-$GD_2$ IgM antibody is from clone 126.

* * * * *